United States Patent [19]

Eibl et al.

[11] Patent Number: 5,776,452
[45] Date of Patent: Jul. 7, 1998

[54] THROMBOSIS AGENT

[75] Inventors: Johann Eibl, Vienna; Anton Philapitsch, Ebenfurt; Hans Peter Schwarz, Vienna, all of Austria

[73] Assignee: Immuno Aktiengesellschaft, Vienna, Austria

[21] Appl. No.: 410,766

[22] Filed: Mar. 27, 1995

[30] Foreign Application Priority Data

Mar. 30, 1994 [DE] Germany ............... 44 11 143.6

[51] Int. Cl.$^6$ ............... A61K 38/48; A61K 35/14; A61K 35/16
[52] U.S. Cl. ............... 424/94.64; 424/94.63; 424/529; 424/530; 424/531
[58] Field of Search ............... 424/94.64, 94.2, 424/94.6, 94.63, 529–531

[56] References Cited

U.S. PATENT DOCUMENTS

| | | | |
|---|---|---|---|
| 4,178,368 | 12/1979 | Heimburger et al. | 424/94.3 |
| 4,645,668 | 2/1987 | Pinnell | 424/94.2 |
| 4,774,087 | 9/1988 | Wu et al. | 424/94.64 |
| 4,808,405 | 2/1989 | Smith et al. | 424/94.3 |
| 5,116,615 | 5/1992 | Gokcen et al. | 424/94.2 |
| 5,304,383 | 4/1994 | Eibl et al. | 424/499 |
| 5,520,912 | 5/1996 | Eibl et al. | 424/94.64 |

FOREIGN PATENT DOCUMENTS

| | | |
|---|---|---|
| 0 307 847 | 3/1989 | European Pat. Off. . |
| 0 159 311 | 4/1989 | European Pat. Off. . |
| 0 310 065 | 4/1989 | European Pat. Off. . |
| 0 480 906 | 4/1992 | European Pat. Off. . |
| 0 353 218 | 5/1992 | European Pat. Off. . |
| 0 337 817 | 1/1994 | European Pat. Off. . |
| 2387241 | 12/1978 | France . |
| 580 963 | 10/1976 | Switzerland . |
| 93/07893 | 4/1993 | WIPO . |

OTHER PUBLICATIONS

Gonzales–Gronow et al., "Mechanism of Activation of Human Plasminogen by the Activator Complex, Streptokinase Plasmin", Jul. 25, 1977, pp. 1090–1094.

V. V. Kakkar et al., "Intermittent Plasminogen—Streptokinase Treatment of Deep Vein Thrombosis", 1988, pp. 127–138.

A. Schoppmann et al., "Production and Quality Assurance of LYS–Plasminogen Steam Treated", Feb. 2, 1988, pp. 157–163.

Yumiko Takada et al., "The Conversion of Streptokinase—Plasminogen Complex to SK–Plasmin Complex in the Presence of Fibrin or Fibrinogen", Jul. 2, 1989, pp. 133–139.

*Primary Examiner*—Leon B. Lankford, Jr.
*Assistant Examiner*—Christopher R. Tate
*Attorney, Agent, or Firm*—Foley & Lardner

[57] ABSTRACT

The invention provides compositions having thrombolytic effects, and comprise plasmin and a plasminogen activator. Such compositions can be administered locally or systemically. The invention also provides simple and safe therapies for thrombotic states and prevention of such states.

19 Claims, No Drawings

THROMBOSIS AGENT

DESCRIPTION

The invention relates to a pharmaceutical composition with thrombolytic effect (thrombosis agent).

By thrombosis a pathological blood coagulation within vessels which leads to the obstruction of a vessel, mostly of veins, but also of arteries, is understood. As a consequence, signs of vascular congestion such as blue discoloration or edema as well as pain and malaise appear in venous thrombosis. Thrombosis is particularly dangerous due to the danger of further transport of clots to organs such as kidney, brain or lung (embolism).

The causes of thromboses are damage of the vessel wall which lead to the accumulation of thrombocytes as well as impairments of the regulation of blood coagulation (for example through a deficiency of anti-thrombin III) as well as changes in the flow properties of blood with vortex formation and circulation obstruction such as, for example, those which can occur during prolonged periods of immobility.

The treatment of thrombosis can be carried out via 2 different ways, namely (1) by medicinal dissolution of the clot (by thrombolysis) and (2) by a surgically operative procedure, especially with non-dissolvable clots. Obviously, in addition to this, the possibility of a combination of (1) and (2) also exists.

The medicinal dissolution referred to as (1) above, i.e. thrombolytic therapy, presents itself especially for the treatment of patients who tend to thromboses. Intravascular fibrin is thereby dissolved and the thrombus is made smaller or is eliminated. In this connection, the success of a thrombolytic therapy depends not least on prompt dissolution of the thrombus so that the perfusion of a blood vessel can be restored at the earliest possible time point.

Venous and arterial thrombi which originate embolically or at the place of the thrombotic obstruction of a blood vessel contain fibrin. This fibrin can be lysed by the fibrinolytically active enzyme plasmin, whereby the thrombus is dissolved.

Plasmin is the term for the proteolytic enzyme, a serine proteinase, that can disintegrate blood clots comprising fibrin to soluble products (fibrinopeptides),and hence is active as a fibrinolytic agent (thrombolytic agent). When required plasmin is generated at the site of the blood clot from the inactive precursor plasminogen, i.e. the zymogen of plasmin, which is present at a concentration of about 200 mg/ml blood plasma.

The activation of plasminogen to plasmin occurs through various plasma factors or through special plasminogen activators belonging to the serine proteinases, such as urokinase or tissue-PA (tPA, tissue plasminogen activator), which is also identical with the vessel wall-PA. tPA possesses a molecular weight of 72,000 and is composed of various structural elements (domains) which are stabilized through disulfide bridges, namely a finger, growth factor, two kringel and a serine proteinase domain. With the aid of the kringel domains, tPA binds to the fibrin clot and is activated by this to cleave the plasminogen also bound there.

For example streptokinase, an exogenous activator from Streptococci which itself possesses neither kinase-typical nor proteolytic activity, acts enzymatically upon plasminogen only after complex formation with plasminogen (J. Biol. Chem. 253 (1987) 1090–1094).

It is therefore customary during thrombolytic therapy to administer an enzyme that acts as a plasminogen activator; such a so-called thrombolytically active enzyme can be, for example, tPA, urokinase, pro-urokinase, streptokinase or staphylokinase.

V. V. Kakkar and F. M. Scully, Haemostasis 18: Suppl. 1 (1988) 127–138 describe the thrombolytic treatment of patients by an infusion of plasminogen and a subsequent infusion of streptokinase for the activation of the plasminogen in vivo; for comparison, patients were treated with streptokinase alone. It was shown by this that the consecutive administration of plasminogen and plasminogen activator was superior to the sole administration of streptokinase.

The administration of lys-plasminogen instead of the native glu-plasminogen for the thrombolytic therapy is proposed by A. Schoppmann et al., Haemostasis 18: Suppl. 1 (1988) 157–163. Lys-plasminogen is a general term used in the literature for proteolytically modified forms of the native plasminogen (glu-plasminogen) which are obtained therefrom through the cleavage of a polypeptide from the $NH_2$-terminus. Up to now, lysine, methionine and valine have been detected as N-terminal amino acids of the species of lys-plasminogen known today. In contrast to the molecular weight of glu-plasminogen, which lies at 90,000–94,000, values of about 80,000 are cited for lys-plasminogen. Lys-plasminogen has the advantage that it adsorbs on fibrin with a higher affinity and can be more quickly converted with a plasminogen activator to plasmin. Lys-plasminogen is produced from plasma for example and treated for virus inactivation in order to exclude the transmission of infectious agents.

The combined administration of plasminogen with a plasminogen activator can, however, also occur in the form of a complex of both components. Y. Takada and A. Takada, Thrombosis Research 54 (1989) 133 to 139, describe the formation of an equimolar complex of streptokinase and plasminogen. This complex leads to a quicker formation of plasmin in the presence of fibrin. In the absence of fibrin or fibrinogen, however, only a slow and inadequate conversion of the streptokinase-plasminogen complex to a streptokinase-plasmin complex is achieved.

A complex of plasminogen and a plasminogen activator, namely staphylokinase, is also known from EP-B-0337817. The complex is produced and isolated in an equimolar ratio, whereby no more free staphylokinase is present. Partial conversion of plasminogen to plasmin is achieved by the complex formation, for which reason a staphylokinase/plasminogen (plasmin) complex is effectively present.

When a direct administration of the fibrinolytically active enzyme plasmin is desired, the plasminogen is converted in vitro to plasmin in this way. Thereby, to prevent autolytic degradation, plasmin is usually stabilized through the addition of conventional stabilizers. The production of plasmin can be carried out for example as described in WO-A-93/07893. Plasminogen is brought into contact with an immobilized plasminogen activator in order to obtain the active plasmin in this manner; in doing so, attempts are made to ensure that the plasmin preparation no longer contains any plasminogen activator.

The object of the present invention is to provide a plasmin-containing pharmaceutical preparation with improved thrombolytic effect which is simple and cost effective to produce and can be applied in a simple and safe manner.

This object is solved with the present invention.

The present invention includes a pharmaceutical composition for thrombolytic therapy comprising plasmin and a plasminogen activator, wherein the plasminogen activator is selected from the group consisting of tissue plasminogen activator and urokinase. The composition can be in solution or in a lyophilized state.

Preferably, at least a portion of the plasminogen activator is in a non-complexed, free form. Preferably, at least 30%, and more preferably, at least 50% of the plasminogen activator is in a non-complexed free form. The plasmin can be fibrinolytically active. The pharmaceutical composition can further comprise at least one protein selected from the group consisting of lys-plasminogen, pro-urokinase, and streptokinase.

The composition can be made by mixing (optionally including incubation) plasminogen and a plasminogen activator only a short period of time prior to administration of the mixture, which contains the plasmin that results from the reaction of plasminogen with the plasminogen activator. Additionally, plasmin can be directly mixed with the plasminogen activator. The plasminogen and/or plasmin and plasminogen activator can be mixed together by a device introduced at the site of administration. Such mixing can occur in the channels of the device.

Compositions according to the invention can have various plasmin to plasminogen activator ratios. For example, compositions can have molar ratios of plasmin to plasminogen activator of one mole plasmin to a range of 0.01 to 3 moles of plasminogen activator, or other ratios.

The invention also pertains to methods of treating thrombosis, methods of preventing embolisms or thromboembolic conditions in mammals and the like, comprising administering to a mammal a pharmaceutical composition containing plasmin and a plasminogen activator, wherein the plasminogen activator is selected from the group consisting of tissue plasminogen activator and urokinase. The methods of the invention can employ the above-described compositions. The compositions can be administered with a cannula, catheter or other implements.

By plasmin, an "active plasmin" according to the invention is thereby understood, i.e. a fibrinolytically active plasmin, for example, a plasmin obtainable in vitro from its zymogen plasminogen and optionally stabilized.

Surprisingly, it was found that the composition according to the invention, which aside from plasmin comprises a plasminogen activator in at least partially free form, demonstrates an excellent thrombolytic activity which is superior to the effect to be attained by sole use of plasmin.

This was not to be expected based for example on the above named state of the art, according to which for example streptokinase, an exogenous activator, actively acts upon plasminogen only after complex formation with plasmin (ogen).

It is therefore possible with the composition according to the invention to exploit not only the direct fibrinolytic effect of (active) plasmin, but also the sustained promoting effect of a plasminogen activator which can easily activate the endogenous plasminogen present in the body and/or in the thrombus based on its at least partially unbound, hence non-complex bound, form. It must be seen as surprising that the composition according to the invention which comprises plasmin and a plasminogen activator, which is present in at least partially free form, leads to substantially more effective results and above all to a quicker thrombolysis in comparison to a sole application of plasmin.

It was also determined on patients with cerebral blood clots that the composition according to the invention significantly improves the success rate of a thrombolytic therapy.

The composition according to the invention can be systemically or locally applied, for example directly at the site of the thrombosis and/or embolism.

It is preferable according to the invention to apply the preparation directly at the site of the thrombosis and/or embolism, for example with the aid of a catheter which is introduced in the corresponding blood vessel, for example intra-arterial. In this manner, side effects which can be connected with a systemic administration of plasmin can be avoided.

Therefore, subject matter of the invention is also the use of a composition comprising plasmin and plasminogen activator according to the invention for the systemic or preferably local application (at the site of the thrombosis and/or embolism) in the treatment and prevention of thrombosis and/or embolism and related manifestations.

Further subject matter of the invention is the use of plasmin together with plasminogen activator for the production of an application system, for example a medicament, for the systemic or preferably local application in the treatment and prevention of thrombosis and/or embolism and related manifestations.

Further subject matter of the invention is the use of a composition according to the invention or of plasmin and plasminogen activator for the production or making available of an application system, for example based on a device for local application in the treatment and prevention of thrombosis and embolism and similar manifestations.

Subject matter of the invention is also a method for the treatment and prevention of thrombolytic manifestations in mammals (human and animal) according to which a composition according to the invention or the components plasmin, plasminogen activator and optionally plasminogen (s) are systemically or locally applied, for example at the site of the thrombosis and/or embolism. Preferably, the treatment is carried out before, during or after a course of thrombolytic therapy.

The plasminogen activator is employed according to the invention in at least partially free form, hence not entirely as complexes with plasmin and/or plasminogen.

Preferably, the device for the local application is a cannula or a catheter for introduction in a blood vessel. Such a cannula or catheter can be a cannula or catheter commonly used for introduction in a blood vessel with a customary form suitable for this and of a customary material suitable for this.

The device which is preferably a cannula or a catheter for introduction in a blood vessel can contain the composition according to the invention or the components plasmin, plasminogen activator or the corresponding starting materials for their production. Alternatively and preferably, the composition or application system according to the invention, for example the components plasminogen and/or plasmin as well as plasminogen activator, are led, simultaneously or in succession, through the device, especially cannula or catheter, wherein the device is preferably introduced into the body in such a way that the composition or the application system according to the invention reaches the site of the thrombosis or its immediate surroundings.

Preferably, the composition according to the invention also additionally comprises one or several plasminogens, and especially, a lys-plasminogen.

The same is true for the use of the individual components plasmin and plasminogen activator; preferably, one or several plasminogens are also additionally co-employed here, wherein the application can occur preferably simultaneously or, however, also in any short successive order.

As carriers and/or adjuvants for the pharmaceutical composition or as a carrier (liquid) for the application of the individual components, pharmaceutical vehicles, diluents and/or adjuvants generally known and customary for compositions and applications of this type are suitable.

The following given preferred amounts and quantitative proportions of plasmin, plasminogen activator and/or plasminogens refer to the pharmaceutical composition according to the invention, but also to the application of the individual components, for example in the use according to the invention together with a device, preferably a cannula or catheter, to be introduced at the site of the thrombosis and/or embolism.

The molar proportion, plasmin/plasminogen activator, preferably amounts to 1/0.01 to ⅓.

Plasmin and tPA are preferably employed in the ratio of 1:0.1 to 1:1000, and particularly 1:0.5 to 1:125, and primarily of about 1:4 (CU/µg).

The unit, CU, corresponds thereby to the caseinolytic activity of plasmin that cleaves fragments from casein which are soluble in trichloroacetic acid and are calculable through spectrophotometric determination of the extinction at 280 nm.

The detection for a plasminogen activator in free and/or non-complexed form in plasmin preparations can thereby occur through customary methods such as, for example, through gel chromatography, SDS electrophoresis (under non-reducing conditions) or through adsorption of the plasmin on immobilized lysine.

When, according to the invention, one or several plasminogens are also used in addition to the plasmin and plasminogen activator, then the molar ratio of plasmin to plasminogens preferably amounts to 1:0.01 to 1:1.

The composition according to the invention comprises the plasmin preferably in an amount of 1 to 95 parts by weight with respect to the weight of the entire composition and, especially, in an amount of 10 to 30 parts by weight.

The amounts of plasminogen activator and optionally additional plasminogens are established from the above named preferred quantitative proportions.

The dosage of the composition according to the invention to be administered in the systemic as well as the local application is determined by the severity of the condition, the general state of health of the patient and also especially by the thrombosis history, i.e. for example by the frequency and the characteristics of previously occurring thrombotic manifestations.

The same is also true for an application of the individual components, for example in a use according to the invention together with a catheter or a cannula.

As a plasminogen activator, an activator, a combination and/or a chimera can be employed, preferably selected from the group tPA, urokinase, pro-urokinase and streptokinase. The plasminogen activators are present in the composition according to the invention at least partially in non-complexed form.

The composition according to the invention can take place according to a known method customarily used for these types of compositions by mixing of the components plasmin, plasminogen activator and optionally one or several plasminogens in a vessel suitable for this, preferably when being stirred. Depending on the intended form of administration, the mixing can occur in the diluent (solvent) already suitable as a carrier, for example for an infusion solution, or can however also occur in a pharmaceutically acceptable solvent, optionally together with other adjuvants and/or carriers for subsequent stabilization. The preparation obtained in this manner or the mixture to be further processed is preferably stabilized by the addition of a suitable known stabilizer such as, for example, phospholipids, carbohydrates, albumin; depending on the desired form of administration, still further method steps can then follow the production through mixing and subsequent stabilization, such as for example preferably lyophilization.

Surprisingly it was found that the incubation of plasmin and/or plasminogen with a plasminogen activator for the production of the composition according to the invention can be performed in a simple manner; this incubation is usually of very short duration such that extensive complex formation is avoided. This is particularly surprising because, as was indicated by way of introduction in the discussion of the state of the art, certain exogenous activators, for example streptokinase, act enzymatically upon plasminogen only after complex formation.

Therefore, the composition according to the invention is optimally formed only shortly before its intended administration in the course of thrombolytic therapy or it can be formed during thrombolytic therapy, especially then when it is applied for example in the form of an infusion solution or together with a device, for example, a cannula or a catheter, to be introduced at the site of the thrombosis. Based on the short reaction time, the preparation according to the invention can thereby be produced even during the thrombolytic therapy, for example within a device introduced at the site of the thrombosis, for example a cannula or a catheter, to which according to the invention the individual components can be supplied simultaneously or quickly one after the other, especially in a diluent suitable therefor. The influx in the device (catheter or cannula) should occur thereby preferably with such a speed that a reaction time of at least 30 sec., and especially of at least 1 minute, hence a sufficient reaction time, is attained until the composition, i.e. the then already finished preparation according to the invention, reaches the site of the application.

As stated above, lys-plasminogen is especially used when the composition according to the invention is produced through reaction of a plasminogen and a plasminogen activator. The plasminogen is preferably virus inactivated. The plasminogen is brought into contact with a plasminogen activator and preferably incubated at a temperature of 15° to 37° C., and especially at room temperature, usually for at least 30 sec. and preferably at least 1 minute until the attainment of a desired plasmin activity.

The incubation time is determined not only by the amount of the plasminogen and the plasminogen activator, but also for example by the degree of the complex formation with the plasminogen activator which, however, preferably should be avoided as far as possible according to the invention.

Optimization experiments have shown that at least 50% of the employed lys-plasminogen (in a concentration of 25 CU/ml) with 100 µg tPA/ml (proportion of CU/µg=1:4) is already converted to active plasmin after 2 minutes incubation time at 37° C. The rate of formation of plasmin can be accelerated thereby through a corresponding increase in the concentration of the lys-plasminogen and/or by tPA.

In the framework of the present invention, a kit in the form of a package unit is also made available for the production of the composition according to the invention or the application of the individual components according to the invention together with a suitable device to be introduced at the site of the thrombosis which is especially suitable for the production of the preparation according to the invention shortly before the systemic or especially before local application. The kit consists of at least 2 containers which each comprise at least one of the component(s) necessary for the production of the preparation according to the invention or the application according to the invention. A container comprises thereby, for example, active plasmin-forming component(s) or already active, preferably stabilized plasmin or the zymogen of the plasmin, i.e. plasminogen, preferably lys-plasminogen, and the other container comprises as a second component the plasminogen activator which is present in at least partially free form non-complexed with plasmin.

However, the kit can also consist of 3 containers of which each container comprises a component from the group plasmin, plasminogen activator and plasminogen(s).

In a further embodiment, the kit can consist of 2 containers of which one comprises active plasmin and the other the components plasminogen(s) and plasminogen activator.

The invention is now more closely illustrated through the following Examples without limiting it to them.

EXAMPLES

Determination of the caseinolytic plasmin activity Casein is provided as a 4% solution in a phosphate buffer (67 mM, pH 7.4). 2.0 ml casein solution are mixed with 1.6 ml of the phosphate buffer and 0.4 ml of the sample and incubated 30 minutes at 37° C. Thereafter, the non-cleaved casein is precipitated by addition of 6 ml 15% trichloroacetic acid. The extinction at 280 nm is measured in the supernatant. The caseinolytic activity is calculated according to the following formula:

$E280 \times 16.3 \times$ dilution of the sample$=CU/ml$.

Determination of the amidolytic plasmin activity

The chromogenic substrate S 2403 (firm: Chromogenix) is amidolytically cleaved by plasmin. Thereby, p-nitroaniline is released which can be measured spectrophotometrically as extinction at 405 nm. The measured values are evaluated by comparison with a plasmin standard (plasmin, firm: Chromogenix).

Example 1

A composition according to the invention is produced. Lys-plasminogen produced according to EP 0353218 underwent virus inactivation treatment according to EP 0159311 and was then incubated with tPA (Actilyse, Boehringer Mannheim) in 0.5 mM Tris/NaCl buffer (pH=7.4).

In a test tube, equal amounts of each of the solutions of the two components were mixed in various concentrations. The concentration of lys-plasminogen in the incubation mixture amounted to 1.6, 6.2, 12.5, 25 and 50 CU/ml.

The amount of tPA was selected in such a way that a ratio of CU/µg of 1:4 was set. The incubation time amounted to 2 and/or 6 min. Thereafter, the plasmin activity was amidolytically determined. The results are entered in the following Table.

TABLE

| Production of active plasmin in the presence of tPA. | | | |
|---|---|---|---|
| Lys-plasminogen | tPA | plasmin/lys-plasminogen (%) after incubation period of | |
| (CU/ml) | (µg/ml) | 2 min | 6 min |
| 1.6 | 6.4 | 15 | 43 |
| 6.2 | 24.8 | 30 | 69 |
| 12.5 | 50 | 51 | 69 |

TABLE-continued

| Production of active plasmin in the presence of tPA. | | | |
|---|---|---|---|
| Lys-plasminogen | tPA | plasmin/lys-plasminogen (%) after incubation period of | |
| (CU/ml) | (µg/ml) | 2 min | 6 min |
| 25 | 100 | 55 | 64 |
| 50 | 200 | 88 | 56 |

Example 2

In a further test, the preparation according to the invention was produced by continuous incubation. 2500 CU lys-plasminogen in 25 ml Ringer solution and 50 mg tPA in 125 ml Ringer solution were prepared. The solutions were simultaneously introduced in the same ratio in a catheter which is customarily used for the medicinal application of pharmaceutical preparations in blood vessels. The catheter was 1.5 m long and had a volume of 0.5 ml. The flow-through rate amounted to 30 ml per second. The plasmin activity was amidolytically determined after the exit of the solution.

The continuous preparation of the preparation was observed over a period of 45 min. It was shown that the conversion of plasminogen into plasmin in the presence of tPA was almost complete (98.6%) during the entire observation period.

Example 3

A course of thrombolytic therapy was carried out with a composition according to the invention freshly produced according to Example 1. 20 patients with carotid embolism were treated in a study by local administration of the preparation according to the invention, and for comparison to this, with a plasminogen activator alone. A mixture of freshly produced active plasmin and tPA (Actilyse, firm: Boehringer Mannheim) was employed as the preparation according to the invention. 2500 CU lys-plasminogen (Immuno AG) and 10 mg tPA each per 25 ml 0.9% NaCl solution were simultaneously and parallel administered in the same ratio over 2 infusion pumps to a microcatheter for an hour. For comparison, tPA (20 ml per 2 hours) was infused alone. At the site of the thrombosis, the thrombolysis was monitored by means of diagnostic angiography in 15 min. intervals.

It was shown that the preparation according to the invention resulted in complete thrombolysis after an average of 45 min. in 8 of 9 cases. The comparative experiment with sole use of tPA showed that the lysis was complete in only 8 of 11 cases, although the treatment duration was twice as long; the average lysis time of 103 min., hence more than twice as long.

We claim:

1. A pharmaceutical composition for thrombolytic therapy comprising active plasmin and a plasminogen activator selected from the group consisting of tissue plasminogen activator and urokinase, wherein the active plasmin and plasminogen activator are present in the range of 10 CU plasmin per microgram plasminogen activator to 1 CU plasmin per milligram plasminogen activator and at least a portion of the plasminogen activator is present in a non-complexed, free form.

2. The pharmaceutical composition according to claim 1, further comprising at least one protein selected from the group consisting of lys-plasminogen, pro-urokinase, and streptolinase.

3. The pharmaceutical composition according to claim 1, wherein the composition is in a lyophilized state.

4. A method of treating thrombotic disorders in a mammal, comprising:

administering to a mammal a pharmaceutical composition comprising active plasmin and a plasminogen activator selected from the group consisting of tissue plasminogen activator and urokinase, wherein the active plasmin and plasminogen activator are present in the range of 10 CU plasmin per microgram plasminogen activator to 1 CU plasmin per milligram plasminogen activator and at least a portion of the plasminogen activator is present in a non-complexed, free form.

5. The method according to claim 4, wherein the composition is administered to the patient immediately after mixing plasminogen and the plasminogen activator together.

6. The method according to claim 4, wherein plasminogen and the plasminogen activator are mixed together by a device introduced at the site of administration.

7. The method according to claim 6, wherein the mixing occurs in a channel of the device.

8. The method according to claim 4, further comprising at least one protein selected from the group consisting of lys-plasminogen, pro-urokinase, and streptokinase.

9. The method according to claim 4, wherein the pharmaceutical composition is administered with a cannula or catheter.

10. A method of preventing embolisms in a mammal, comprising:

administering to a mammal a pharmaceutical composition comprising active plasmin and a plasminogen activator selected from the group consisting of tissue plasminogen activator and urokinase, wherein the active plasmin and plasminogen activator are present in the range of 10 CU plasmin per microgram plasminogen activator to 1 CU plasmin per milligram plasminogen activator and at least a portion of the plasminogen activator is present in a non-complexed, free form.

11. The method according to claim 10, wherein the composition is administered to the patient immediately after mixing plasminogen and the plasminogen activator together.

12. The method according to claim 10, wherein plasminogen and the plasminogen activator are mixed together by a device introduced at the site of administration.

13. The method according to claim 12, wherein the mixing occurs in a channel of the device.

14. The method according to claim 10, further comprising at least one protein selected from the group consisting of lys-plasminogen, pro-urokinase, and streptokinase.

15. The method according to claim 10, wherein the pharmaceutical composition is administered with a cannula or catheter.

16. A method of treating thrombotic and embolic manifestations, comprising administering active plasmin and a plasminogen activator selected from the group consisting of tissue plasminogen activator and urokinase to a mammal in need of treatment, wherein the active plasmin and plasminogen activator are present in the range of 10 CU plasmin per microgram plasminogen activator to 1 CU plasmin per milligram plasminogen activator and at least a portion of the plasminogen activator is present in a non-complexed, free form.

17. The method according to claim 16, wherein the administration is local.

18. The method according to claim 16, wherein the administration is systemic.

19. The method according to claim 16, wherein the administration is intra-arterial.

\* \* \* \* \*